United States Patent
Dondio et al.

(10) Patent No.: US 6,262,104 B1
(45) Date of Patent: Jul. 17, 2001

(54) DIARYLALKENYLAMINE DERIVATIVES

(75) Inventors: Giulio Dondio; Silvano Ronzoni, both of Milan (IT)

(73) Assignee: SmithKline Beecham p.l.c., Brentford (GB)

(*) Notice: Subject to any disclaimer, the term of this patent is extended or adjusted under 35 U.S.C. 154(b) by 0 days.

(21) Appl. No.: 09/029,892

(22) PCT Filed: Sep. 9, 1996

(86) PCT No.: PCT/EP96/03988

§ 371 Date: Jun. 5, 1998

§ 102(e) Date: Jun. 5, 1998

(87) PCT Pub. No.: WO97/10230

PCT Pub. Date: Mar. 20, 1997

(30) Foreign Application Priority Data

Sep. 15, 1995 (IT) ............................................. MI95A1930

(51) Int. Cl.[7] ................. A61K 207/401; A61K 31/166; A61P 25/04; C07C 237/30; C07D 207/09
(52) U.S. Cl. ............... 514/408; 514/210.01; 514/211.01; 514/231.2; 514/239.5; 514/277; 514/357; 514/374; 514/378; 514/472; 514/617; 514/618; 514/620; 514/624; 540/484; 540/544; 546/106; 546/152; 546/162; 546/329; 546/337; 548/215
(58) Field of Search .................................... 564/374, 383; 548/578; 560/37, 38, 41; 514/408, 533, 539, 648

(56) References Cited

U.S. PATENT DOCUMENTS 4,514,414 * 4/1985 Bondinell et al. ................. 514/422
4,564,685 1/1986 Findlay et al. ..................... 548/578

FOREIGN PATENT DOCUMENTS

| 0 000 322 | 1/1979 | (EP) . |
| 0 085 959 | 8/1983 | (EP) . |
| 0 219 756 | 4/1987 | (EP) . |
| WO 90/15599 | 12/1990 | (WO) . |

* cited by examiner

*Primary Examiner*—Jane C. Oswecki
(74) *Attorney, Agent, or Firm*—Soma Simon; William King; Charles Kinzig

(57) ABSTRACT

Compounds, or solvates or salts thereof, of formula (I):

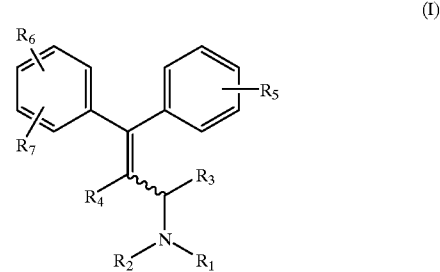

selective delta opioid agonists and antagonists and may be of therapeutic utility as analgesics, immunosuppressants to prevent rejection in organ transplant and skin graft, antiallergic and anti-inflammatory agents, brain cell protectants, agents for treating drug and alcohol abuse, gastritis, diarrhoea, cardiovascular and respiratory diseases, cough, mental illness, epilepsy and, in general, agents for the treatment of those pathological conditions which, customarily, can be treated with agonists and antagonists of the delta opioid receptor.

8 Claims, No Drawings

DIARYLALKENYLAMINE DERIVATIVES

This application is a 371 of PCT/EP96/03988 filed Sep. 9, 1996.

This invention is concerned with novel diarylalkenylamine derivatives, processes for their preparation, and their use in medicine.

The presence of at least three populations of opioid receptors (mu, delta and kappa) is now well established and documented and all three appear to be present in the central and peripheral nervous system of many species including man (Lord J. A. H. et al, *Nature* 1977, 267, 495).

Activation of al three opioid receptor subtypes can lead to antinociception in animal models. In particular, studies with peptidic delta agonists have indicated that activation of the delta receptor produces antinociception in rodents, primates and can induce clinical analgesia in man (D. E. Moulin et al, *Pain,* 1985, 23, 213). Evidence exists that suggest a lesser propensity of delta agonists to cause the usual side-effects associated with mu and kappa activation (Galligan et al., *J. Pharm. Exp. Ther.,* 1984, 229, 641).

Substituted diarylalkenylamines useful as analgesics (moffet R. B. and Everson G. N. *Org. Prep. and Procedures,* 53, 11, 1979), antidepressant agents [Jones et al. *J. Med. Chem.* 161, 14, 1971; Astra Lakemedel AB (Jpn. Kokai, Tokkyo Koho, 80/11, 563); Astra Lakemedel AB (Jpn. Kokai, Tokkyo Koho, 79/39,057)] and as potential inhibitors of adrenal corticosteroid biogenesis (blank B. et al. *J. Med. Chem.,* 271, 12, 1969) have been already described.

We have now discovered a novel class of diarylalkenylamine derivatives which are potent and selective delta opioid agonists and antagonists which may therefore be of potential therapeutic utility as analgesics, immunosuppressants to prevent rejection in organ transplant and skin graft, anti-allergic and anti-inflammatory agents, brain cell protectants, agents for treating drug and alcohol abuse, gastritis, diarrhoea, cardiovascular and respiratory diseases, cough, mental illness, epilepsy and, in general, agents for the treatment of those pathological conditions which, customarily, can be treated with agonists and antagonists of the delta opioid receptor.

According to the present invention, there is provided a compound, or a solvate or salt thereof, of formula (I):

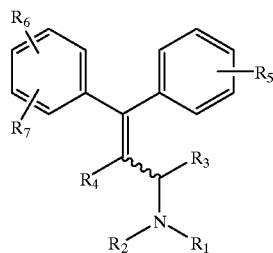

(I)

in which:
- $R_1$ and $R_2$, which can be the same or different, are each hydrogen, linear or branched $C_{1-6}$ alkyl, $C_{3-7}$ cycloalkenyl, $C_{4-6}$ cycloalkylalkyl, $C_{3-6}$ alkenyl, $C_{3-5}$ alkenyl, aryl, aralkyl or furan-2 or 3-yl alkyl or may form together a $C_{3-7}$ alkyl ring which may be interrupted by oxygen.
- $R_3$ and $R_4$, which can be the same or different, are each hydrogen, linear or branched $C_{1-6}$ alkyl;
- $R_5$ is hydroxy, $C_{1-6}$ alkoxy, thiol or alkythio;
- $R_6$ is a —C(Z)—$R_8$ group, in which Z is oxygen or sulphur, $R_8$ is $C_{1-8}$-alkyl, $C_{1-8}$-alkoxy or $NR_9R_{10}$, wherein $R_9$ and $R_{10}$, which may be the same or different, are hydrogen, straight or branched $C_{1-6}$ alkyl, $C_{3-7}$ cycloalkyl, $C_{4-6}$ cycloalkylalkyl, $C_{3-6}$ alkenyl, aryl or aralkyl, or $R_6$ is a 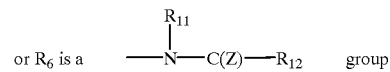 group in which $R_{11}$ and $R_{12}$ have the same meaning as $R_9$ and $R_{10}$ or together form an optionally substituted heterocyclic ring and Z is as defined above, and $R_7$ is hydrogen, straight or branched $C_{1-8}$ alkyl or halogen, preferably chlorine.

Preferably, $R_6$ is in the para or meta position.

Examples of $R_1$ and $R_2$ are methyl and, taken together, pyrrolidinyl.

Examples of $R_3$ and $R_4$ are hydrogen.

Examples of $R_5$ are hydroxy and methoxy.

Examples of $R_6$ are $CONEt_2$, $CON(—NH_2—)_4$ and $CON(i-Pr)_2$.

An example of $R_7$ is hydrogen.

A first group of preferred compound of formula (I) are those in which each of $R_3$ and $R_4$ is hydrogen or $C_{1-6}$ alkyl, preferably methyl and $R_1$, $R_2$, $R_5$, $R_6$ and $R_7$ are as defined above for formula (I).

A second preferred group of compounds of formula (I) are those in which $R_5$ is an hydroxy or $C_{1-6}$ alkoxy group, preferably methoxy, $R_1$, $R_2$, and $R_6$ and $R_7$ are as defined above for formula (I) and each of $R_3$ and $R_4$ is hydrogen or $C_{1-6}$ alkyl.

A particularly preferred group of compounds of formula (I) are those in which $R_6$ is a group —C(Z)—R8 where $R_8$ is $NR_9R_{10}$, $R_9$ and $R_{10}$ being as defined above for formula (I), Z is oxygen, $R_1$, $R_2$ and $R_7$ are as defined above for formula (I), each of $R_3$ and R4 is hydrogen or $C_{1-6}$ alkyl, and $R_5$ is hydroxy or $C_{1-6}$ alkoxy.

The compounds of formula (I) or their salts or solvates are preferably in pharmaceutically acceptable or substantially pure form. By pharmaceutically acceptable form is meant, inter alia, of a pharmaceutically acceptable level of purity excluding normal pharmaceutical additives such as diluents and carriers, and including no material considered toxic at normal dosage levels.

A substantially pure form will generally contain at least 50% (excluding normal pharmaceutical additives), preferably 75%, more preferably 90% and still more preferably 95% of the compound of formula (I) or its salt or solvate.

One preferred pharmaceutically acceptable form is the crystalline form, including such form in a pharmaceutical composition. In the case of salts and solvates the additional ionic and solvent moieties must also be non-toxic.

Examples of pharmaceutically acceptable salts of a compound of formula (I) include the acid addition salts with the conventional pharmaceutical acids, for example, maleic, hydrochloric, hydrobromis, phosphoric, acetic, fumaric, salicylic, citric, lactic, mandelic, tartaric, succinic, benzoic, ascorbic and methanesulphonic.

The compounds of formula (I) exist in tow geometric isomer forms, E and Z, and the invention extends to all such forms as well as to their mixtures thereof.

In addition, the compounds of formula (I) may exist in more than one stereoisomeric form, and the invention extends to all such forms as well as to their mixtures thereof, including racemates.

The invention also provides a process for the preparation of a compound of formula (I) which comprises reacting a compound of general formula (IV)

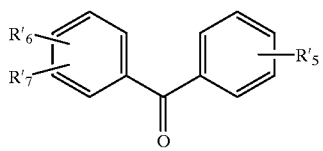

in which R'$_5$ to R'$_7$ are R$_5$ to R$_7$ as defined for formula (I) or a group or atom convertible to R$_5$ to R$_7$, with an ylide of general formula R$_1$R$_2$NCH$_2$CH$_2$P$^+$Rh$_3$Br$^-$ (A) or with a phosphonate of general formula (EtO)$_2$POCH(R$_4$)—COOEt (B) or (EtO)$_2$POCH2—COR$_3$ (C) in the presence of a base to form a compound of general formula (Ia)

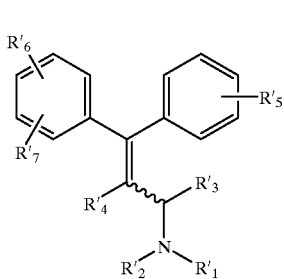

in which R'$_1$ to R'$_4$ are R$_1$ to R$_4$ as defined in formula (I), or a group or atom convertible to R$_1$ to R$_4$; with the following provisos:

when a compound of general formula (IV) is treated with the phosponate of general formula (B), the resulting ester derivative undergoes a subsequent reduction to the corresponding alcohol which, after activation with a suitable leaving group, is treated with an amine of general formula NHR$_1$R$_2$ in which R$_1$ and R$_2$ are as defined above to give a compound of general formula (Ia);

when a compound of general formula (IV) is treated with a phosponate of general formula (C), the resulting ketone intermediate undergoes a subsequent reductive amination using an amine of general formula NHR$_1$R$_2$ in which R$_1$ and R$_2$ are as defined above to give a compound of general formula (Ia), and optionally thereafter, performing one or more of the following steps:
a) where R'$_1$ to R'$_7$ are R$_1$ to R$_7$, converting anyone of R'$_1$ to R'$_7$ to R$_1$ to R$_7$ to obtain a compound of general formula (I);
b) where R'$_1$ to R'$_7$ are other than R$_1$ to R$_7$, converting anyone of R$_1$ to R$_7$ to another R$_1$ to R$_7$ to obtain compound of general formula (I);
c) forming a salt and/or solvate of the compound of formula (I)

In general, compounds of formula (I) may be prepared by the methods illustrated in the following general reaction schemes, or by modification thereof, using readily available starting materials, reagents and conventional synthetic procedures. If a particular enantiomer of a compound of the present invention is desired, it may be synthesised starting from the desired enantiomer of the starting material and performing reactions not involving racemization processes or it may be prepared by chiral synthesis. or by derivation with a chiral auxillary, where the resulting diastereomeric mixture is separated and the auxillary group cleaved to provide the pure desired enantiomers. Alternatively, compounds of formula (I) can be separated into their enantiomers by forming diastereomeric salts with an appropriate optically active acid, followed by fractional crystallization resolution and subsequent recovery of the pure enantiomers. If a particularly geometric isomer, E or Z, is desired, it may be preferentially synthesised using conventional synthetic procedures or, it may be separated by conventional chromatographic or crystallization techniques from a mixture of the two E/Z isomers.

Synthesis of compounds of general formula (IV) is described in Scheme 1. The ketones (IV) are obtained by treating an aromatic aldehyde (II) with a lithium derivative (III). The resulting carbinol is oxidised using a PDC in CH$_2$Cl$_2$ or, alternatively, using the Swern procedure.

Scheme 1

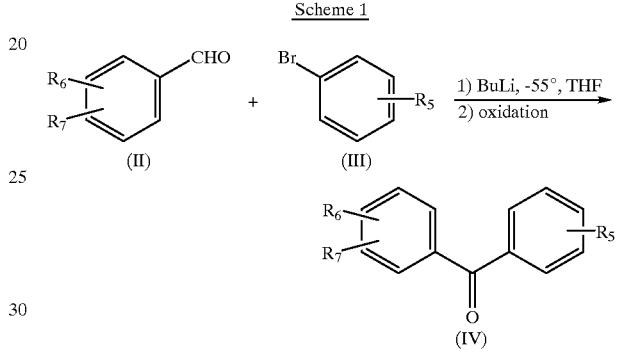

Compounds of general formula (I) in which R$_3$ and R$_4$ are hydrogen, may be obtained by treating ketones of general formula (IV) with ylides of triphenylphosphonium as described in Scheme 2:

Scheme 2

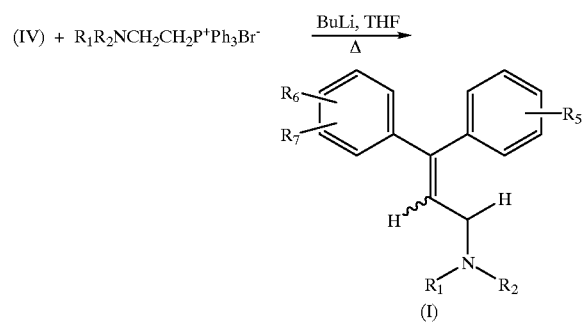

Compounds of general formula (I), in which R$_4$=Me, may be prepared following Wittig procedures starting from ketones of general formula (IV) and substituted phosphonate salts to obtain the unsaturated esters of general formula (V). Subsequent reduction using NaBH$_4$ in t-BuOH/MeOH gives the allyl alcohols of general formula (VI) which may be transformed to the compounds of general formula (I) via mesylate using the appropriate substituted amine (see Scheme 3).

Scheme 3

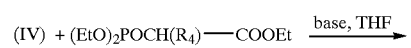

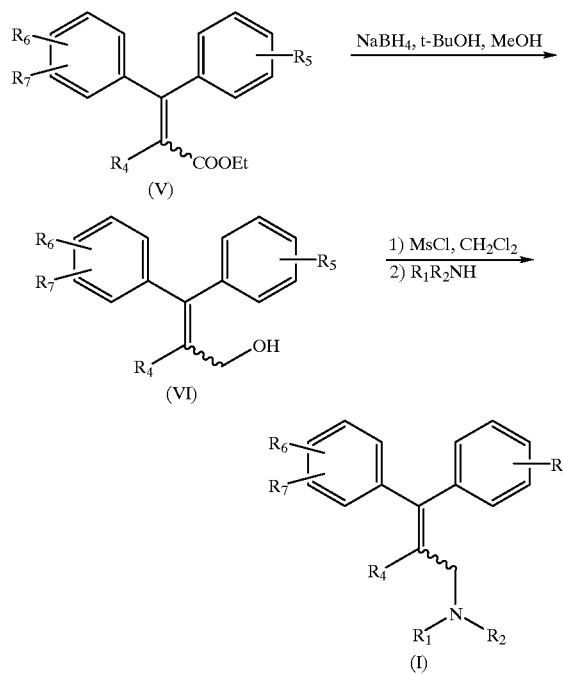

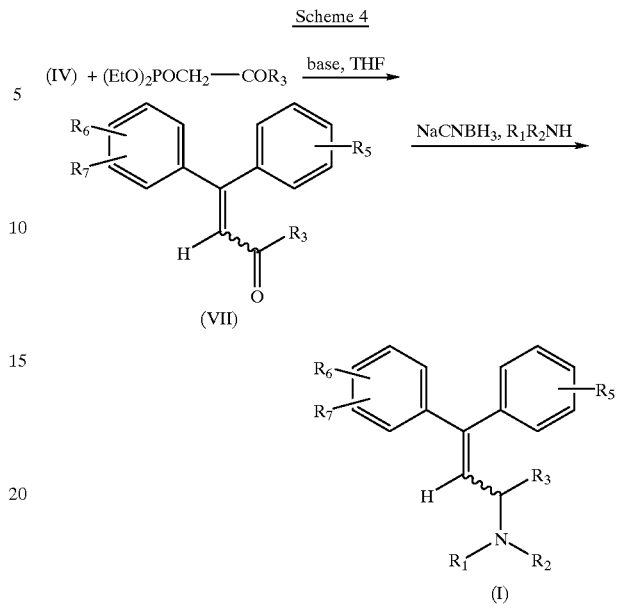

Compounds of general formula (I), in which R₃=Me, may be prepared following Horner-Emmons procedures starting from ketones of general formula (IV) and substituted phosphonate salts to obtain the unsaturated ketones of general formula (VII), which may be transformed to the compounds of general formula (I) via reductive amination using the appropriate substituted amine and a suitable hydride such as NaCNBH₃ (see Scheme 4).

If the groups R₆ in the general formula (I), are not chemically compatible with the above reaction schemes (for example if they are $C_{1-8}OOC$— or $C_{1-8}CO$—), the final compounds of general formula (I') and (I") may be obtained by transformation of the corresponding amides (R₆= CONR₉R₁₀) into the related acid [compounds of formula (VIII)] by hydrolysis. The resulting acids may be converted into the acyl chlorides via SOCl₂ or (COCl)₂ in CH₂Cl₂ and then treated with the appropriate alcohols to obtain esters of general formula (I') or with the appropriate dialkylzinc derivatives to obtain ketones of general formula (I").

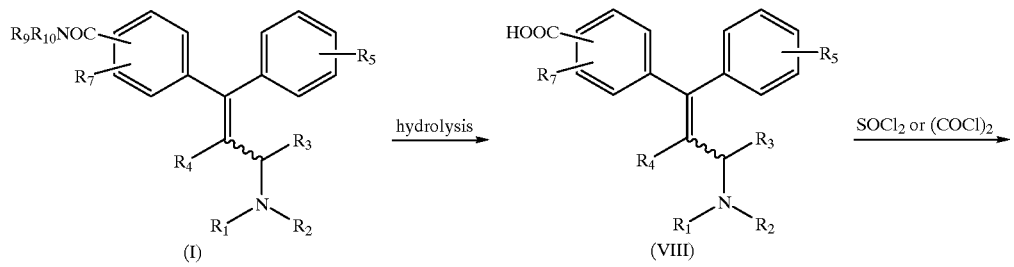

Scheme 5

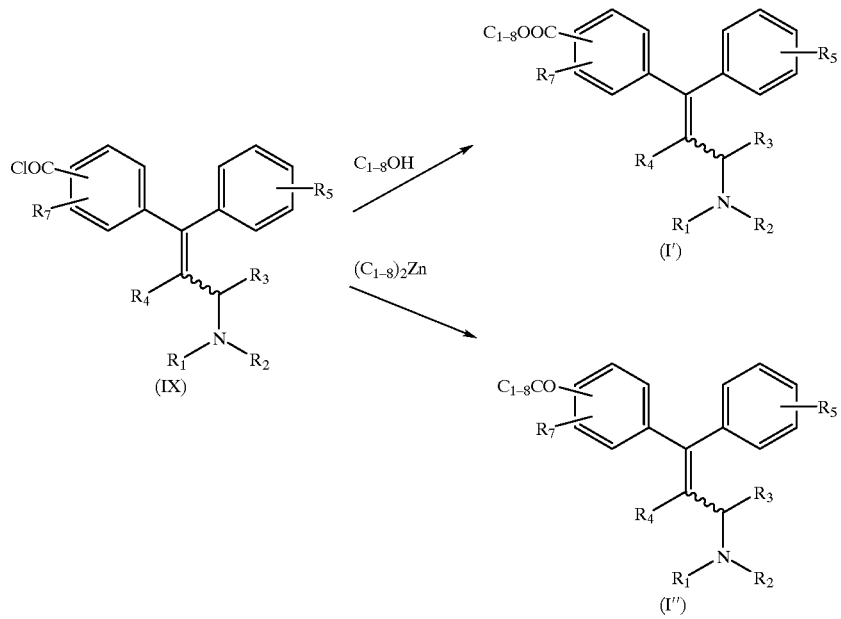

Compounds of general formula (I''') in which $R_5$ is a MeO group, may be demethylated, for example, using $BBr_3$ in $CH_2Cl_2$ as solvent or alternatively, using $(CH_3)_3SiCl/NaI$ in boiling $CH_3CN$, to obtain other compounds of general formula (I) in which $R_5$ is OH, as shown in Scheme 6.

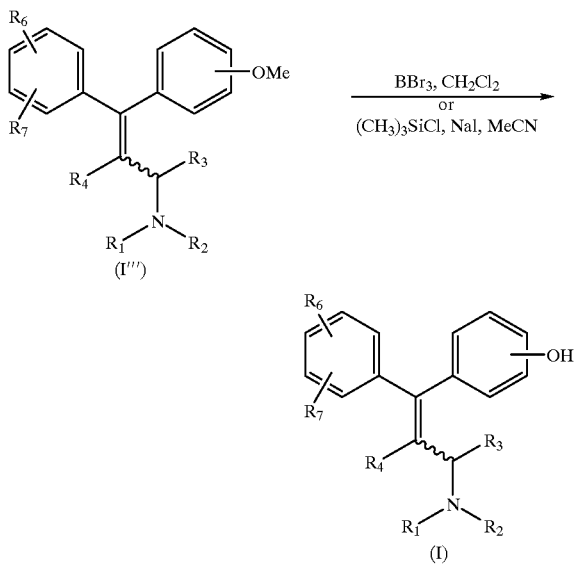

The compounds of formula (I) may be converted into their pharmaceutically acceptable salts by reaction with the appropriate organic or mineral acids.

Solvates of the compounds of formula (I) may be formed by crystallization or recrystallization from the appropriate solvent. For example, hydrates may be formed by crystallization or recrystallization from aqueous solutions, or solutions in organic solvents containing water.

Also salts or solvates of the compounds of formula (I) which are not pharmaceutically acceptable may be useful as intermediates in the production of pharmaceutically acceptable salts or solvates. Accordingly such salts or solvates also form part of this invention.

In general compounds of formula (I) acting as selective delta receptor ligands may be useful as analgesics, immunosuppressants to prevent rejection in organ transplant and skin graft, anti-allergic and anti-inflammatory agents, brain cells protectant, for the treatment of drug and alcohol abuse, to decrease gastric secretion, for the treatment of diarrhoea, cardiovascular and respiratory diseases, cough, mental illness, epileptic seizures and other neurologic disorders (herein after referred to as the 'Conditions'). In particular, the activity of the compounds of formula (I) as delta agonists in standard tests indicates that they are of potential therapeutic utility as analgesic agents for the amelioration or elimination of pain.

Accordingly the present invention also provides a compound of formula (I), or a pharmaceutically acceptable salt or solvate thereof, for use as an active therapeutic substance.

The present invention further provides a pharmaceutical composition comprising a compound of formula (I), or a pharmaceutically acceptable salt or solvate thereof, and a pharmaceutically acceptable carrier.

The present invention also provides the use of a compound of formula (I), or a pharmaceutically acceptable salt or solvate thereof, in the manufacture of a medicament for the treatment of the Conditions.

Such a medicament, and a composition of this invention, may be prepared by admixture of compound of the invention with an appropriate carrier. It may contain a diluent, binder, filler, disintegrant, flavouring agent, colouring agent, lubricant or preservative in conventional manner.

These conventional excipients may be employed for example as in the preparation of compositions of known agents for treating the conditions. Preferably, a pharmaceutical composition of the invention is in unit dosage form and in a form adapted for use in the medical or veterinarial fields. For example, such preparations may be in a pack form accompanied by written or printed instructions for use as an agent in the treatment of the conditions.

The suitable dosage range for the compounds of the invention depends on the compound to be employed and on the condition of the patient. It will also depend, inter alia, upon the relation of potency to absorbability and the frequency and route of administration.

The compound or composition of the invention may be formulated for administration by any route, and is preferably in unit dosage form or in a form that a human patient may administer to himself in a single dosage. Advantageously, the composition is suitable for oral, rectal, topical, parenteral, intravenous or intramuscular administration. Preparations may be designated to give slow release of the active ingredient.

Compositions may, for example, be in the form of tablets, capsules, sachets, vials, powders, granules, lozenges, reconstitutable powders, or liquid preparations, for example solutions or suspensions, or suppositories.

The compositions, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable setting agents such as sodium lauryl sulphate.

Solid compositions may be obtained by conventional methods of blending, filling, tabletting or the like. Repeated blending operations may be used to distribute the active agent throughout those compositions employing large quantities of fillers. When the composition is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The composition may also be in the form of an ingestible capsule, for example of gelatin containing the compound, if desired with a carrier or other excipients.

Compositions for oral administration as liquids may be in the form of, for example, emulsions, syrups, or elixirs, or may be presented as a dry product for reconstitution with water or other suitable vehicle before use. Such liquid compositions may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; aqueous or non-aqueous vehicles, which include edible oils, for example almond oil, fractionated coconut oil, oily esters, for example esters of glycerine, or propylene glycol, or ethyl alcohol, glycerine, water or normal saline; preservatives, for example methyl or propyl p-hydroxybenzoate or sorbic acid; and if desired conventional flavouring or colouring agents.

The compounds of this invention may also be administered by a non-oral route. In accordance with routine pharmaceutical procedure, the compositions may be formulated, for example for rectal administration as a suppository. They may also be formulated for presentation in an injectable form in an aqueous or non-aqueous solution, suspension or emulsion in a pharmaceutically acceptable liquid, e.g. sterile pyrogen-free water or a parenterally acceptable oil or a mixture of liquids. The liquid may contain bacteriostatic agents, anti-oxidants or other preservatives, buffers or solutes to render the solution isotonic with the blood, thickening agents, suspending agents or other pharmaceutically acceptable additives. Such forms will be presented in unit dose form such as ampoules or disposable injection devices or in multi-dose forms such as a bottle from which the appropriate dose may be withdrawn or a solid form or concentrate which can be used to prepare an injectable formulation.

The compound of this invention may also be administered by inhalation, via the nasal or oral routes. Such administration can be carried out with a spray formulation comprising a compound of the invention and a suitable carrier, optionally suspended in, for example, a hydrocarbon propellant.

Preferred spray formulations comprise micronised compound particles in combination with a surfactant, solvent or a dispersing agent to prevent the sedimentation of suspended particles. Preferably, the compound particle size is from about 2 to 10 microns.

A further mode of administration of the compounds of the invention comprises transdermal delivery utilising a skin-patch formulation. A preferred formulation comprises a compound of the invention dispersed in a pressure sensitive adhesive which adheres to the skin, thereby permitting the compound to diffuse from the adhesive through the skin for delivery to the patient. For a constant rate of percutaneous absorption, pressure sensitive adhesives known in the art such as natural rubber of silicone can be used.

As mentioned above, the effective dose of compound depends on the particular compound employed, the condition of the patient and on the frequency and route of administration. A unit dose will generally contain from 20 to 1000 mg and preferably will contain from 30 to 500 mg, in particular 50, 100, 150, 200, 250, 300, 350, 400, 450, or 500 mg. The composition may be administered once or more times a day for example 2, 3 or 4 times daily, and the total daily dose for a 70 kg adult will normally be in the range of 100 to 3000 mg. Alternatively the unit dose will contain from 2 to 20 mg of active ingredient and be administered in multiples, if desired, to give the preceding daily dose.

No unacceptable toxicological effects are expected with compounds of the invention when administered in accordance with the invention.

The present invention also provides a method for the treatment and/or prophylaxis of the Conditions in mammals, particularly humans, which comprise administering to the mammal in need of such treatment and/or prophylaxis an effective amount of a compound of formula (I) or a pharmaceutically acceptable salt or solate thereof.

The activity of the compounds of the present invention as selective delta ligands is determined in radioligand binding assays as described below.

Mouse brain membranes were prepared as described by Kosterlitz (*Br. J. Pharmacol.*, 1981, 73, 939.). The binding of the preferential delta ligand [$^3$H]-[D-ala$^2$.D-Leu$^5$]-enkephalin (DAMGO) was evaluated at its $K_D$ concentration (1.3 nM) in presence of 40 nM of the unlabelled mu ligand [D-ala$^2$, MePhe$^4$, Gly-ol$^5$]-enkephalin (DAMGO). The binding of the mu ligand [$^3$H]-DAMGO (*Eur. J. Pharmacol.*, 1989, 166, 213) and of the kappa ligand [$^3$H]-U69593 (*Excerpta Medica*, 1990, 211) were carried out at 0.5 nM. The non-specific binding was determined in presence of naloxone (10 $\mu$M) for all tritiated ligands. Binding data were expressed as percentage of inhibition and fitted the following equation: f(x)=100·X/(IC$_{50}$+X) where X are cold drug concentration values. The IC$_{50}$ obtained were used to calculate the inhibitory constants (K$_i$) accordingly to the Cheng and Prusoff relation (*Biochem. Pharmacol.*, 1973, 22, 3099).

The delta agonist/antagonist activity of the compounds of the present invention is determined in the mouse vas deferens (MVD) bioassay as described below.

Vasa deferentia were obtained from CD-1 mice and were suspended in a Mg$^{2+}$- free Krebsa buffer at 37° C. The tissues were electrically stimulated with pulse trains having the following parameters: train duration 50 ms, stimulus duration 2 ms, frequency of stimuli 50 Hz, maximal voltage 60–70 V, train frequency 0.1 Hz. Concentration response curves for each compounds were constructed cumulatively. Linear regression analysis and IC$_{50}$ concentrations were evaluated according to Talarida and Murray (*Manual of Pharmacological Calculations*, Springer Verlag NY, 1981).

The most potent compounds described in the present invention showed affinities for the delta receptor ranging from 0.5 to 200 nM with delta selectivity ranging from 10 to 1500 times in respect to the other opioid receptor types. These compounds displayed also potent delta agonist or antagonist properties in the MVD preparation. Selective delta agonists (antagonised by the selective delta antagonist naltrindole) displayed IC50s ranging from 1 to 500 nM. As examples, compound of Example 2 shows a Kiδ=2.5 nM; Kiμ/Kiδ=350 and Kiκ/Kiδ=2500; in the MVD bioassay it displays an IC50=30 nM.

Mouse abdominal constriction (MAC) (Proc. Soc. Exp. Biol. Med., 1957, 95, 729), mouse tail-flick (MTF) (*J. Pharm. Exp. Ther.*, 1941, 72, 74) and mouse tail-flick warm water (MTF-WW) (*Life Sci.*, 1986, 39, 1795) tests were adopted to evaluate the antinociceptive activity of the compounds of the present invention.

The following Preparations illustrate the synthesis of intermediates, whereas the Procedures A, B, and C illustrate the preparation of compounds of the present invention here described for selected Examples. These compounds are summarised in the chemical Table 1 along with the synthetic method used for every Example. The analytical data are summarised in Table 2.

PREPARATION 1
N,N-Diethyl-4-(3-methoxybenzoyl)benzamide 60 ml (96 mmol) of a 1.6 N solution of n-butyllithium in n-hexane were added slowly, under a nitrogen atmosphere and at −55° C., to a solution of 18 g (96 mmol) of 3-bromoanisole in 200 ml of dry THF. After 2 h the solution was added via cannula to a solution of 19.7 g (96 mmol) of N,N-diethyl-4-formylbenzamide in 200 ml of dry THF. The reaction mixture was allowed to warm up to room temperature overnight, then it was quenched with NH$_4$Cl saturated solution. The aqueous phase was extracted with Et$_2$O. The organic phase dried over Na$_2$SO$_4$ and the solvent removed in vacuo. The crude reaction mixture was employed in the next synthetic step without further purification. A solution of 15.3 ml of DMSO in 45 ml of CH$_2$Cl$_2$ was added slowly, under a nitrogen atmosphere and at −55 ° C., to a solution of 9 ml of oxalyl chloride in 200 ml of CH$_2$Cl$_2$. After 2 min. the crude reaction mixture obtained in the preceding step and dissolved in 90 ml of CH$_2$Cl$_2$ was added, followed, after 15 min. by 65 ml of Et$_3$N. The reaction mixture was allowed to warm up to room temperature in 2 h, then it was quenched with 500 ml of H$_2$O. The organic phase is separated and washed with 10% HCl solution, then dried over Na$_2$SO$_4$ and the solvent removed in vacuo. The crude reaction mixture was purified by flash chromatography, eluting with Et$_2$O/hexane 9:1 respectively, yielding 12.5 g of the title compound.
IR cm$^{-1}$ (KBr): 2980, 1660, 1620, 1580.
MS (EI) m/z: 312.0 (M+1).
N.M.R. 300 MHz (CDCl$_3$): δ7.8 (m, 2H); 7.5–7.1 (m, 6H); 3.8 (s, 3H); 3.5 (m, 2H); 3.2 (m, 2H); 1.2 (m, 6H).

Two other compounds were obtained analogously:
N-[4-(3-methoxybenzoyl)benzoyl]pirrolidine I.R. cm$^{-1}$ (KBr): 2980, 2880, 1660, 1620.

N,N-Diisopropyl-4-(3-methoxybenzoyl)benzamide I.R. cm$^{-1}$ (KBr): 2970, 2840, 1665, 1620.

PREPARATION 2
(E,Z)-N,N-Diethyl-4-[[2-ethoxycarbonyl-1-(3-methoxyphenyl)]-1-ethenyl]benzamide 2.1 g (52 mmol) of a 60% mineral oil suspension of NaH were suspended in 100 ml of dry THF under a nitrogen atmosphere. The mixture was cooled to 5° C. and 10.3 ml (52 mmol) of triethylphosphonoacetate were added. After 15 min. a solution of 5.4 g (17.3 mmol) of N,N-diethyl-4-(3-methoxybenzoyl)benzamide in 50 ml of dry THF was added. The reaction mixture was refluxed 8 h, then poured into H$_2$O and extracted with AcOEt. The organic phase was dried over Na$_2$SO$_4$ and the solvent removed in vacuo. The crude reaction mixture was purified by flash chromatography, eluting with Et$_2$O/hexane 9:1 respectively, yielding 5.9 g of the title compound. IR cm$^{-1}$ (neat): 2980, 1720, 1630, 1425 cm$^{-1}$. MS (EI) m/z: 380.1 (M−1) N.M.R. 300 MHz (CDCl$_3$): δ7.4–7.2 (m, 5H); 6.9–6.7 (m, 3H); 6.35 (s, 1H); 4.1 (q, 2H); 3.8 (s, 3H); 3.6–3.2 (m, 4H); 1.3–1.1 (m, 9H).

PREPARATION 3
(E,Z)-N,N-Diethyl-4-[[3-hydroxy-1-(3-methoxyphenyl)]-1-propenyl]benzamide 7.2 g (19 mmol) of (E,Z)-N,N-diethyl-4-[[2-ethoxycarbonyl-1-(3-methoxyphenyl)]-1-thenyl]benzamide were dissolved in 90 ml of tert-butanol under a nitrogen atmosphere. 1.1 g (28 mmol) of NaBH$_4$ were added and the reaction mixture brought to reflux. 15.4 ml of MeOH were added during the course of 1 h and, after refluxing 2 h, the reaction mixture was quenched with H$_2$O and the solvent removed in vacuo. The residue was taken up in H$_2$O end extracted with AcOEt. then the organic phase was dried over Na$_2$SO$_4$ and the solvent removed in vacuo. The crude reaction mixture was purified by flash chromatography, eluting with ET$_2$O, yielding 2.5 g of the title compound. IR cm$^{-1}$ (neat): 3400, 2980, 1620, 1430 cm$^{-1}$. MS (EI) m/z: 339.1 N.M.R. 300 MHz (CDCl$_3$): δ7.5–7.1 (m, 5H); 6.9–6.6 (m, 3H); 6.25 (m, 1H); 4.2 (m, 2H); 3.8 (s, 3H); 3.6–3.2 (m, 4H); 1.3–1.1 (m, 6H).

METHOD A
(E,Z)-N,N-Diethyl-4-[[1-(3-methoxyphenyl)-3-pyrrolidin-1-yl]-1-propenyl]benzamide

EXAMPLE 1

0.9 ml (6.6 mmol) of Et$_3$N and 0.5 ml (6.6 mmol) of methanesulfonylchloride dissolved in 5 ml of CH$_2$Cl$_2$ were added, under a nitrogen atmosphere and at 10° C., to a solution of 1.4 g (4.1 mmol) of (E,Z)-N,N-diethyl-4-[[3-hydroxy-1-(3-methoxyphenyl)]-1-propenyl]benzamide in 14 ml of CH$_2$Cl$_2$. After 90 min the reaction mixture was poured onto H$_2$O and the organic phase was washed with a saturated NaCl solution and dried over Na$_2$SO$_4$. The solvent was removed in vacuo and the residue was dissolved in 15 ml of toluene. 1.6 ml of pyrrolidine were added and the reaction mixture was heated to 90° C. overnight. The solvent was removed in vacuo, the resulting residue was brought to acidic pH with a 5% HCl solution and the aqueous phase was extracted with Et$_2$O, then brought to basic pH with a 15% NaOH solution and extracted AcOEt. The organic phase was dried over Na$_2$SO$_4$ and the solvent removed in vacuo. The crude reaction mixture was purified by flash chromotagraphy, eluting with a mixture CH$_2$Cl$_2$/MeOH/conc. NH$_4$OH 90:7:0.7 respectively, yielding 1.2 g of the title compound.

METHOD B
(E)-N,N-Diethyl-4-[[1-(3-hydroxyphenyl)-3-pyrrolidin-1-yl]-1-propenyl]benzamide citrate

EXAMPLE 2
and (Z)-N,N-Diethyl-4-[[1-(3-hydroxyphenyl)-3-pyrrolidin-1-yl]-1-propenyl]benzamide citrate

EXAMPLE 3

1.7 ml (18.3 mmol) of boron tribromide were dissolved in 45 ml of dry $ChCl_3$ under a nitrogen atmosphere. 1.2 g (3.0 mmol) of (E,Z)-N,N-diethyl-4-[[1-(3-methoxyphenyl)-3-pyrrolidin-1-yl]-1-propenyl]benzamide dissolved in 20 ml of dry $CHCl_3$ were added dropwise at room temperature. After 2 h the solution was poured onto 50 g of crushed ice containing 5 ml of conc. $NH_4OH$. The resulting mixture was stirred for 20 min, then the phases were separated and the aqueous phase extracted with $CH_2CL_2$. The combined organic extracts were dried over $Na_2SO_4$ and the solvent removed in vacuo. The crude reaction mixture was purified by flash chromatography, eluting a mixture $CH_2Cl_2$/MeOH/conc. $NH_2OH$ 86:10:0.6 respectively, yielding 0.9 g of the product with greater Rf, identified as (E)-N,N-diethyl-4-[[1-(3-hydroxyphenyl)-3-pyrrolidin-1-yl]-1-propenyl]benzamide. This product was dissolved in a mixture acetone/MeOH; an equimolar amount of anhydrous citric acid was added, the solvent was removed in vacuo and the resulting solid was triturated with Et2O, yielding 1.1 g of the desired product. Continuing the eluition, 0.36 g of the product with smaller Rf were obtained, identified as (Z)-N,N-diethyl-4-[[1-(3-hydroxyphenyl)-3-pyrrolidin-1-yl]-1-propenyl]benzamide. This product was dissolved in a mixture acetone/MeOH; an equimolar amount of anhydrous citric acid was added, the solvent was removed in vacuo and the resulting solid was triturated with $ET_2O$, yielding 0.43 g of the desired product METHOD C
(E,Z)-N,N-Diethyl-4-[[3-dimethylamino-1-(3-methoxyphenyl)]-1-propenyl]benzamide citrate

EXAMPLE 4

8 ml (11.3 mmol) of a 1.4 N solution of n-butyllithium in hexane were added dropwise, at room temperature and under a nitrogen atmosphere, to a suspension of 4.67 g (11.3 mmol) of dimethylaminoethyltriphenylphosphonium bromide in 30 ml of dry THF. After 20 min a solution of 1.17 g (3.8 mmol) of N,N-diethyl-4-(3-methoxybenzoyl)benzamide in 10 ml of dry THF was added. The reaction mixture was refluxed for 4 h, then it was poured in $H_2O$. The phases were separated and the aqueous layer was extracted with AcOEt. The organic phase was dried over $Na_2SO_4$ and the solvent removed in vacuo. The crude reaction mixture was purified by flash chromatography, eluting with a mixture $CH_2Cl_2$/MeOH/conc. $NH_4OH$ 90:7:0.7 respectively, yielding 1.1 g of the title product as a free base. 0.3 g of product were dissolved in a mixture acetone/MeOH: and equimolar amount of anhydrous citric acid was added, the solvent was removed in vacuo and the resulting solid was triturated with Et2O, yielding 0.25 g of the title product.

TABLE 1

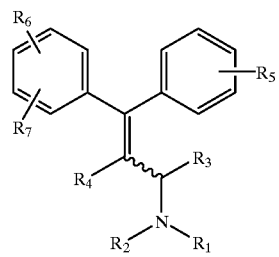

| Example | Method | Name | $R_1$ | $R_2$ | $R_3$ | $R_4$ | $R_5$ | $R_6$ | $R_7$ |
|---|---|---|---|---|---|---|---|---|---|
| 1 | A | (E,Z)-N,N-Diethyl-4-[[1-(3-methoxyphenyl)-3-pyrrolidin-1-yl]-1-propenyl]benzamide | —$(CH_2)_4$— | | H | H | OMe | p-$CONEt_2$ | H |
| 2 | B | (E)-N,N-Diethyl-4-[[1-(3-hydroxyphenyl)-3-pyrrolidin-1-yl]-1-propenyl]benzamide citrate | —$(CH_2)_4$— | | H | H | OH | p-$CONEt_2$ | H |
| 3 | B | (Z)-N,N-Diethyl-4-[[1-(3-hydroxyphenyl)-3-pyrrolidin-1-yl]-1-propenyl]benzamide citrate | —$(CH_2)_4$— | | H | H | OH | p-$CONEt_2$ | H |
| 4 | C | (E,Z)-N,N-Diethyl-4-[[3-dimethylamino-1-(3-methoxyphenyl)]-1-propenyl]benzamide citrate | Me | Me | H | H | OMe | p-$CONEt_2$ | H |
| 5 | B | (E)-N,N-Diethyl-4-[[3-dimethylamino-1-(3-hydroxyphenyl)]-1-propenyl]benzamide | Me | Me | H | H | OH | p-$CONEt_2$ | H |
| 6 | B | (Z)-N,N-Diethyl-4-[[3-dimethylamino-1-(3-hydroxyphenyl)]-1-propenyl]benzamide citrate | Me | Me | H | H | OH | p-$CONEt_2$ | H |
| 7 | C | (E,Z)-1-[4-[[3-Dimethylamino-1-(3-methoxyphenyl)]-1-propenyl]benzoyl]pyrrolidine | Me | Me | H | H | OMe | p-$CON(CH_2)_4$ | H |
| 8 | B | (E)-1-[4-[[3-Dimethylamino-1-(3-hydroxyphenyl)]-1-propenyl]benzoyl]pyrrolidine citrate | Me | Me | H | H | OH | p-$CON(CH_2)_4$ | H |
| 9 | B | (Z)-1-[4-[[3-Dimethylamino-1-(3-hydroxyphenyl)]-1-propenyl]benzoyl]pyrrolidine citrate | Me | Me | H | H | OH | p-$CON(CH_2)_4$ | H |
| 10 | C | (E,Z)-N,N-Diisopropyl-4-[[3-dimethylamino-1-(3-methoxyphenyl)]-1-propenyl]benzamide | Me | Me | H | H | OMe | p-CON(i-Pr)$_2$ | H |
| 11 | B | (E)-N,N-Diisopropyl-4-[[3-dimethylamino-1-(3-hydroxyphenyl)]-1-propenyl]benzamide | Me | Me | H | H | OH | p-CON(i-Pr)$_2$ | H |
| 12 | B | (Z)-N,N-Diisopropyl-4-[[3-dimethylamino-1-(3-hydroxyphenyl)]-1-propenyl]benzamide | Me | Me | H | H | OH | p-CON(i-Pr)$_2$ | H |

TABLE 2

| Ex. | NMR | MS | IR cm$^{-1}$ (KBr) |
|---|---|---|---|
| 1 | (CDCl$_3$): 7.5–7.1(m, 5H); 6.9–6.6(m, 3H); 6.3(t, 1H); 3.8(s, 3H); 3.7–3.2(m, 4H); 3.2(t, 2H); 2.5(m, 4H); 1.8(m, 4H); 1.2(m, 6H). | 392.2(M+.).EI | 2970, 1630, 1430 (neat) |
| 2 | (CDCl$_3$): 7.4(d, 2H); 7.0(m, 4H); 6.7(d, 1H); 6.4(d, 1H); 6.2(t, 1H); 3.6–3.2(m, 8H); 2.8(m, 6H); 1.8(m, 4H); 1.2(m, 6H). | 378.4(M+.).EI | 3200, 2970, 1630 (free base) |
| 3 | (CDCl$_3$): 7.3–7.1(m, 6H); 6.8(m 1H); 6.4(m 1H); 6.2(t, 1H); 3.7(m, 2H); 3.6–3.2(m, 8H); 2.8(m, 4H); 1.8(m, 4H); 1.2(m, 6H). | 378.0(M+.).EI | 3200, 2970, 1610 |
| 4 | (CDCl$_3$): 7.4–7.1(m, 5H); 7.9–7.6(m, 3H); 6.2(t, 1H); 3.8(s, 3H); 3.6–3.2(m, 4H); 2.9(m, 2H); 2.2(s, 6H); 1.2(m, 6H). | 367(M+1).EI | 2960, 2930, 1630 |
| 5 | (DMSO): 9.3(s, 1H); 7.6(d, 2H); 7.2–7.0(m, 3H); 6.5–6.3(m, 3H); 6.1(t, 1H); 3.5–3.4(m, 4H); 2.9(d, 2H); 2.2(s, 6H); 1.2(m, 6H). | 352(M+.).EI | 3440, 1625, 1590 |
| 6 | (DMSO): 9.5(s, 1H); 7.4–7.2(m, 5H); 6.9(d, 1H); 6.6(m, 2H); 6.2(t, 1H); 3.6 3.0(m, 16H); 1.2–1.0(m, 6H). | 351.8(M+.).EI | 3200, 1610, 1450 (free base) |
| 7 | (CDCl$_3$): 7.5(d, 1H); 7.4(d, 1H); 7.3(d, 1H); 7.2–7.1(m, 2H); 6.8(m, 2H); 6.2(t, 1H); 3.8(s, 3H); 3.7–3.4(m, 4H); 3.0(m, 2H); 2.2(s, 6H); 1.8(m, 4H). | 364.2(M+.).EI | 2980, 1630, 1430 (neat) |
| 8 | (DMSO): 7.7(d 2H); 7.4–7.3(m, 3H); 6.8(d, 2H); 6.6(s, 1H); 6.1(m, 1H); 3.6–3.0(m, 12H); 1.8(m, 4H). | 350.2(M+.).EI | 3200, 2980, 1610 (free base) |
| 9 | (DMSO): 7.7(d 2H); 7.4–7.3(m, 3H); 6.8(d, 1H); 6.6–6.5(m, 2H); 6.1(m, 1H); 3.6–3.0(m, 12H); 1.8(m, 4H). | 350.2(M+.).EI | 3440, 2980, 1610 (free base) |
| 10 | — | — | 2970, 1630, 1440 (free base) |
| 11 | (CDCl$_3$): 7.4–7.3(m, 2H); 7.2–7.1(m, 3H); 6.7(m, 3H); 6.2(m, 1H); 3.8(m, 2H); 3.0(m, 2H); 2.2(d, 6H); 1.5(m, 12H). | 380.2(M+.).EI | 2960, 1620, 1450 (free base) |
| 12 | (CDCl$_3$): 7.3–7.2(m, 4H); 6.85(m, 1H); 6.65(m, 1H); 6.45(m, 1H); 6.1(m, 1H); 3.8(m, 2H); 3.0(m, 2H); 2.2(d, 6H); 1.5(m, 12H). | 380.2(M+.).EI | 2960, 1610, 1450 (free base) |

What is claimed is:

1. A compound, or a solvate or salt thereof, of formula (1):

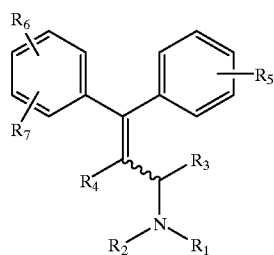

(I)

in which,

R$_1$ and R$_2$, which are the same or different, are each hydrogen, linear or branched C$_{1-6}$ alkyl, C$_{3-7}$ cycloalkyl, C$_{3-7}$ cycloalkenyl, C$_{4-6}$ cycloalkylalkyl, C$_{3-6}$ alkenyl, C$_{3-5}$ alkynyl, aryl, aralkyl or furan-2 or 3-yl alkyl or may form together a C$_{3-7}$ alkyl ring which may be interrupted by oxygen, R$_3$ and R$_4$, which are the same or different, are each hydrogen, linear or branched C$_{1-6}$ alkyl;

R$_5$ is hydroxy, C$_{1-6}$ alkoxy, thiol or alkythio;

R$_6$ is CONEt$_2$, CON(—CH$_2$—)$_4$, or CON(i—Pr)$_2$, and R$_7$ is hydrogen, straight or branched C$_{1-8}$ alkyl or halogen.

2. A compound according to claim 1 in which each of R$_1$ and R$_2$ is methyl or, taken together, for a pyrrolidinyl group.

3. A compound according to claim 1 in which each of R$_3$ and R$_4$ is hydrogen.

4. A compound according to claim 1 in which R$_5$ is hydroxy or methoxy.

5. A compound selected from the group consisting of:

(E,Z)-N,N-Diethyl-4-[[1-(3-methoxyphenyl)-3-pyrrolidin-1-yl]-1-propenyl]benzamide;

(E)-N,N-Diethyl-4-[[1-(3-hydroxyphenyl)-3-pyrrolidin-1-yl]-1-propenyl]benzamide citrate;

(Z)-N,N-Diethyl-4-[[1-(3-hydroxyphenyl)-3-pyrrolidin-1-yl]-1-propenyl]benzamide citrate;

(E,Z)-N,N-Diethyl-4-[[3-dimethylamino-1-(3-methoxyphenyl)]-1-propenyl]benzamide citrate;

(E)-N,N-Diethyl-4-[[3-dimethylamino-1-(3-hydroxyphenyl)]-1-propenyl]benzamide;

(Z)-N,N-Diethyl-4-[[3-dimethylamino-1-(3-hydroxyphenyl)]-1-propenyl]benzamide citrate;

(E,Z)-1-[4-[[3-Dimethylamino-1-(3-methoxyphenyl)]-1-propenyl]benzoyl]pyrrolidine;

(E)-1-[4-[[3-Dimethylamino-1-(3-hydroxyphenyl)]-1-propenyl]benzoyl]pyrrolidine citrate;

(Z)-1-[4-[[3-Dimethylamino-1-(3-hydroxyphenyl)]-1-propenyl]benzoyl]pyrrolidine citrate;

(E,Z)-N,N-Diisopropyl-4-[[3-dimethylamino-1-(3-methoxyphenyl)]-1-propenyl]benzamide;

(E)-N,N-Diisopropyl-4-[[3-dimethylamino-1-(3-hydroxyphenyl)]-1-propenyl]benzamide, and (Z)-N,N-Diisopropyl-4-[[3-dimethylamino-1-(3-hydroxyphenyl)]-1-propenyl]benzamide.

6. A pharmaceutical composition comprising a compound according to claim 1 and a pharmaceutically acceptable carrier.

7. A method for treating a pathological condition mediated by the delta opioid receptor, which comprises administering a compound according to claim 1.

8. A method according to claim 7 for the treatment of pain, organ transplant or skin graft rejection, allergy or inflammation, brain cell degeneration, drug or alcohol abuse, gastritis, diarrhea, cardiovascular or respiratory diseases, cough, mental illness, or epileptic seizures.

* * * * *